United States Patent
Garst et al.

(10) Patent No.: US 6,258,844 B1
(45) Date of Patent: Jul. 10, 2001

(54) CYCLOPENTANE (ENE) OIC ACID, 2-ALKENYL DERIVATIVES AS THERAPEUTIC AGENTS

(75) Inventors: Michael E. Garst, Newport Beach; Michael B. Roof, Los Angeles; Ming F. Chan, Encinitas; David F. Woodward, Lake Forest; Robert M. Burk, Laguna Beach; Todd S. Gac, Costa Mesa; Steven W. Andrews, Rancho Santa Margarita, all of CA (US)

(73) Assignee: Allergan Sales, Inc., Irvine, CA (US)

( * ) Notice: Subject to any disclaimer, the term of this patent is extended or adjusted under 35 U.S.C. 154(b) by 0 days.

(21) Appl. No.: 09/194,457

(22) PCT Filed: May 14, 1997

(86) PCT No.: PCT/US97/08123

§ 371 Date: Nov. 24, 1998

§ 102(e) Date: Nov. 24, 1998

(87) PCT Pub. No.: WO97/45405

PCT Pub. Date: Dec. 4, 1997

Related U.S. Application Data (60) Provisional application No. 60/018,435, filed on May 28, 1996.

(51) Int. Cl.$^7$ .................. A67K 31/215; A61K 31/19
(52) U.S. Cl. .................. 514/530; 514/573; 514/913
(58) Field of Search .................. 514/530, 573, 514/913

(56) References Cited

U.S. PATENT DOCUMENTS 4,994,274   2/1991   Chan et al. .

FOREIGN PATENT DOCUMENTS

| | | |
|---|---|---|
| 0410786 | 1/1991 | (EP) . |
| 0410801 | 1/1991 | (EP) . |
| 0410785 | 7/1991 | (EP) . |
| 88/06448 | 9/1988 | (WO) . |
| 91/19490 | 12/1991 | (WO) . |

OTHER PUBLICATIONS

Bito, L.Z., "Prostaglandins and Related Compounds as Potential Ocular Theraupeutic Agents," *Biological Protection with Prostaglandins*, Cohen, M.M., ed., Boca Raton, Fla, CRC Press, Inc., 1985, pp. 231–252, Chapter 18, vol. I.
Bito, L.Z., "Prostaglandins, Other Eicosanoids, and Their Derivatives as Potential Antiglaucoma Agents," *Applied Pharmacology in the Medical Treatment of Glaucomas* Drance, S.M. and Neufeld, A.H. eds., New York, Grune & Stratton, 1984, pp. 477–505, Chapter 20.
Bito, L.Z., "Prostaglandins, Old Concepts and New Perspectives," Arch. Ophthalmol, 105, 1036 (1987).
Nilsson, et. al., "$PGF_{2\alpha}$ Increases Uveoscleral Outflow," *Invest. Ophthalmol. Vis. Sci.* (suppl), 284, 1987.
Siebold, et.al., "Esterified prostaglandin shows 'potent' promise," *Prodrug* 53, 1989.

*Primary Examiner*—Zohreh Fay
(74) *Attorney, Agent, or Firm*—Robert J. Baran; Carlos A. Fisher; Martin A. Voet (57) ABSTRACT

The invention relates to the use of omega chain modified prostaglandins as ocular hypotensive. The derivatives used in accordance with the invention are encompassed by the following structure formula I:

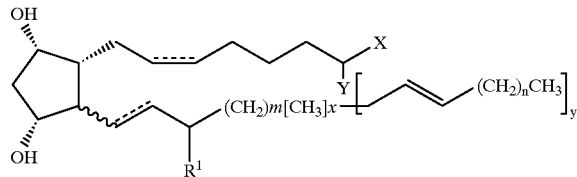

wherein the hatched segments represent α bonds; the wavy segment represents an α or β bond; dashed lines represent a double bond or a single bond; X is selected from the group consisting of —OR and $N(R_2)$; Y is=O or represents 2 hydrogen radicals, provided that Y represents 2 hydrogen radicals when X is OH; R is hydrogen or a lower alkyl radical having up to six carbon atoms; $R_1$ is=O or hydroxy; m is 0, 2, 4 or 6, provided that m is not 4 when the wavy segment represents a β bond; n is 0, 2, 4 or 6; x and y are 0 or 1, provided that x is 1 when y is 0 and y is 1 when x is 0; or 9, 11 and/or 15 ester derivatives of said compound of formula I, e.g. a $C_1$ to $C_6$ alkyl ester derivative; or a pharmaceutically acceptable salt thereof. In a further aspect, the present invention relates to an ophthalmic solution comprising a therapeutically effective amount of a compound of formula (I), wherein the symbols have the above meanings, in admixture with a non-toxic, ophthalmically acceptable liquid vehicle, packaged in a container suitable for metered application.

7 Claims, 3 Drawing Sheets

NaH, THF, 0°C $(CH_3O)_2\overset{O}{\underset{}{P}}\underset{}{\overset{O}{\|}}\underbrace{\hspace{1cm}}(CH_2)_n CH_3$

2a-d  n=0,2,4,6

1. ALIQUOT 336
   NaHCO$_3$, Na$_2$S$_2$O$_4$
   BENZENE:H$_2$O
2. NaBH$_4$, MeOH, 0°C

3a-d  n=0,2,4,6

1. PPTS, MeOH, 40°C
2. LiBH$_4$, Et$_2$O 4a-d  n=0,2,4,6

1. PPTs, MeOH, 40°C
2. $R_2NH, R_2NH \cdot HCl$ 10a, b  R=H,H OR H, CH$_3$

LAH, THF

12a  R=H,H

CYCLOPENTANE (ENE) OIC ACID, 2-ALKENYL DERIVATIVES AS THERAPEUTIC AGENTS

This application claims benefit to U.S. provisional application Ser. No. 60/018,435, filed May 28, 1996.

1. Field of the Invention

The present invention relates to cyclopentane heptenoic acid, 2-alkenyl or alkyl derivatives wherein said alkyl or alkenyl are hydroxy or oxo substituted and substituted in the 1-position with hydroxyl, alkyloxy, amino and amido groups, e.g., the 1-OH derivative of cyclopentane heptenoic acid, 2-alkenyl. These compounds are potent ocular hypotensives, and are particularly suited for the management of glaucoma.

BACKGROUND OF THE INVENTION

2. Description of the Invention

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupillary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe, and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical β-adrenoreceptor antagonists have traditionally been the drugs of choice for treating glaucoma.

Certain eicosanoids and their derivatives have been reported to possess ocular hypotensive activity, and have been recommended for use in glaucoma management. Eicosanoids and derivatives include numerous biologically important compounds such as prostaglandins and their derivatives. Prostaglandins can be described as derivatives of prostanoic acid which have the following structural formula:

Various types of prostaglandins are known, depending on the structure and substituents carried on the alicyclic ring of the prostanoic acid skeleton. Further classification is based on the number of unsaturated bonds in the side chain indicated by numerical subscripts after the generic type of prostaglandin [e.g. prostaglandin E1 ($PGE_1$), prostaglandin $E_2$ ($PGE_2$)], and on the configuration of the substituents on the alicyclic ring indicated by α or β [e.g. prostaglandin $F_{2\alpha}$ ($PGF_{2\alpha}$)].

Prostaglandins were earlier regarded as potent ocular hypertensives; however, evidence accumulated in the last decade, shows that some prostaglandins are highly effective ocular hypotensive agents, and are ideally suited for the long-term medical management of glaucoma. (See, for example, Bito, L. Z. *Biological Protection with Prostaglandins* Cohen, M. M., ed., Boca Raton, Fla, CRC Press Inc., 1985, pp. 231–252; and Bito, L. Z., *Applied Pharmacology in the Medical Treatment of Glaucomas* Drance, S. M. and Neufeld, A. H. eds., New York, Grune & Stratton, 1984, pp. 477–505). Such prostaglandins include $PGF_{2\alpha}$, $PGF_{1\alpha}$, $PGE_2$, and certain lipid-soluble esters, such as $C_1$ to $C_2$ alkyl esters, e.g. 1-isopropyl ester, of such compounds.

Although the precise mechanism is not yet known, experimental results indicate that the prostaglandin-induced reduction in intraocular pressure results from increased uveoscleral outflow [Nilsson et al., *Invest. Ophthalmol. Vis. Sci.* 2 8(suppl), 284 (1987)].

The isopropyl ester of $PGF_{2\alpha}$ has been shown to have significantly greater hypotensive potency than the parent compound, presumably as a result of its more effective penetration through the cornea. In 1987, this compound was described as "the most potent ocular hypotensive agent ever reported." [See, for example, Bito, L. Z., *Arch. Ophthalmol.* 105, 1036 (1987), and Siebold et al., *Prodrug* 5, 3 (1989)].

Whereas prostaglandins appear to be devoid of significant intraocular side effects, ocular surface (conjunctival) hyperemia and foreign-body sensation have been consistently associated with the topical ocular use of such compounds, in particular $PGF_{2\alpha}$ and its prodrugs, e.g. its 1-isopropyl ester, in humans. The clinical potential of prostaglandins in the management of conditions associated with increased ocular pressure, e.g. glaucoma are greatly limited by these side effects.

In a series of co-pending United States patent applications assigned to Allergan, Inc. prostaglandin esters with increased ocular hypotensive activity accompanied with no or substantially reduced side-effects are disclosed. The co-pending U.S. Ser. No. 386,835 (filed Jul. 27, 1989), relates to certain 11-acyl-prostaglandins, such as 11-pivaloyl, 11-acetyl, 11-isobutyryl, 11-valeryl, and 11-isovaleryl $PGF_{2\alpha}$. Intraocular pressure reducing 15-acyl prostaglandins are disclosed in the co-pending application U.S. Ser. No. 357,394 (filed May 25, 1989). Similarly, 11,15- 9,15- and 9,11-diesters of prostaglandins, for example 11,15-dipivaloyl $PGF_{2\alpha}$ are known to have ocular hypotensive activity. See the co-pending patent applications U.S. Ser. Nos. 385,645, 386,312, and 385,834 (all filed on July 27, 1989. The disclosures of these patent applications are hereby expressly incorporated by reference.

SUMMARY OF THE INVENTION

The present invention concerns a method of treating ocular hypertension which comprises administering to a mammal having ocular hypertension a therapeutically effective amount of a compound of formula I wherein the hatched segments represent α bonds; the wavy segment represents an α or β bond; dashed lines represent a double bond or a single bond; X is selected from the group consisting of —OR and $N(R_2)$; Y is=O or represents 2 hydrogen radicals, provided that Y represents 2 hydrogen radicals when X is OH; R is hydrogen or a lower alkyl radical having up to six carbon atoms; $R^1$ is=O or hydroxy; m is 0, 2, 4 or 6, provided that m is not 4 when the wavy segment represents α β bond; n is 0, 2, 4 or 6; x and y are 0 or 1, provided that x is 1 when y is 0 and y is 1 when x is 0; or 9, 11 and/or 15 ester derivatives of said compound of formula I, e.g. a $C_1$ to $C_6$ alkyl ester derivative; or a pharmaceutically acceptable salt thereof.

In a further aspect, the present invention relates to an ophthalmic solution comprising a therapeutically effective amount of a compound of formula (I), wherein the symbols have the above meanings, or a pharmaceutically acceptable salt thereof, in admixture with a non-toxic, ophthalmically acceptable liquid vehicle, packaged in a container suitable for metered application.

In a still further aspect, the present invention relates to a pharmaceutical product, comprising:

a container adapted to dispense its contents in a metered form; and an ophthalmic solution therein, as hereinabove defined.

DETAILED DESCRIPTION OF THE INVENTION

The present invention relates to the use of cyclopentan(ene)oic acid, 2-alkenyl derivatives as therapeutic agents, e.g. as ocular hypotensives. The compounds used in accordance with the present invention are encompassed by the following structural formula I:

wherein the substituents and symbols are as hereinabove defined. As stated above, the dashed lines indicate a single or double bond. The double bonds may be either cis or trans bonds. However, if two solid lines are used at C-13, it indicates a specific configuration for that double bond.

A preferred group of the compounds of the present invention includes compounds that have the following structural formula II:

Another preferred group includes compounds having the formula III:

In the above formulae, the substituents and symbols are as hereinabove defined.

The above compounds of the present invention may be prepared by methods that are known in the art or as shown in the Examples, below. The primary alcohols can be conveniently prepared by reduction of the 1-carboxyl group of the corresponding prostaglandin compounds and the amides can be prepared by amidation of the 1-carboxyl group of the corresponding prostaglandin compounds. In general, the reduction may be performed by chemical reducing agents conventionally used for the conversion of carboxylic acids to alcohols. Chemical reducing agents include, but are not restricted to hydrides, such as lithium aluminium hydride or diisobutylaluminium hydride. As an alternative to direct reduction, the prostaglandin acid may be converted into a corresponding 1-ester before reduction, and the obtained 1-ester may be reduced by chemical reduction. Methods of esterification and reduction of prostaglandin compounds are disclosed in the Examples, below.

The hydroxyl group(s) present in any of the positions 9, 11 and 15 are protected from reduction by protecting groups known in the art.

The secondary and tertiary alcohols are usually prepared from the corresponding primary alcohols via oxidation to aldehydes or ketons and subsequent reaction with a suitable Grignard reagent. These reactions are well known in organic chemistry.

In a preferred group of the compounds of formula (I) the hydroxyl groups in the 9, 11 and/or 15 positions are esterified. Particularly preferred are the 11-esters, 15-esters, 11,15-, 9, 15- and 9,11-diesters. Esterification in these positions may be performed after the reduction of the 1-carboxyl group with appropriate protection.

The above esters according to the present invention can comprise a variety of acyl substituents. In the esters of formula (I) the ester moieties may include an acyclic hydrocarbon radical having from one to twenty carbon atoms, inclusive, preferably are straight or branched-chain alkyl, alkenyl or alkynyl groups of one to ten carbon atoms, such as methyl, ethyl, propyl, butyl, pentyl, etc., or an isomeric form thereof; vinyl, propenyl, etc. Most preferably said hydrocarbon radical is —$CH_3$, —$(CH_2)_3CH_3$, —$CH(CH_3)_2$ or —$C(CH_3)_3$.

Alternatively, the ester moiety can comprise a cyclic component which preferably is a saturated or unsaturated ring having from three to seven carbon atoms; or an aromatic or heteroaromatic ring, preferably having 5 to 10 carbon atoms and containing oxygen, nitrogen or sulfur as a heteroatom, if present. That is, the ester moiety may be phenyl, thienyl, pyridyl, or furyl, or the mono or disubstituted halo, e.g., fluoro or chloro, or C1 to C3 alkyl derivatives, thereof.

The following specific compounds may be utilized in the method of the present invention.

7-[3α–5α-Dihydroxy-2-(6-hydroxy-2E-octenyl) cyclopentyl]-5Z-hepten-1-ol
7-[3α–5α-Dihydroxy-2-(8-hydroxy-4E-decenyl) cyclopentyl]-5Z-hepten-1-ol
7-[3α–5α-Dihydroxy-2-(10-hydroxy-6E-dodecenyl) cyclopentyl]-5Z-hepten-1-ol
7-[3α–5α-Dihydroxy-2-(12-hydroxy-8E-tetradecenyl) cyclopenty]-5Z-hepten-1-ol
7-[3α–5α-Dihydroxy-2-(2-hydroxybutyl)-cyclopentyl]-5Z-hepten-1-ol
7-[3α–5α-Dihydroxy-2-(4-hydroxyhexyl)-cyclopentyl]-5Z-hepten-1-ol
7-[3α–5α-Dihydroxy-2-(8-hydroxydecyl)-cyclopentyl]-5Z-hepten-1-ol
7-[3α–5α-Dihydroxy-2-(8-hydroxydecyl)-cyclopentyl]-5Z-heptenamine
7-[3α–5α-Dihydroxy-2-(8-hydroxydecyl)-cyclopentyl]-5Z-heptenamide
N-Methyl-7-[3α–5α-Dihydroxy-2-(8-hydroxydecyl)-cyclopentyl]-5Z-heptenamide A pharmaceutically acceptable salt is any salt which retains the activity of the parent compound and does not impart any deleterious or undesirable effect on the subject to whom it is administered and in the context in which it is administered. Of particular interest are salts formed with inorganic ions, such as sodium, potassium, calcium, magnesium and zinc.

Pharmaceutical compositions may be prepared by combining a therapeutically effective amount of at least one compound according to the present invention, or a pharmaceutically acceptable salt thereof, as an active ingredient, with conventional ophthalmically acceptable pharmaceutical excipients, and by preparation of unit dosage forms suitable for topical ocular use. The therapeutically efficient amount typically is between about 0.0001 and about 5% (w/v), preferably about 0.001 to about 1.0% (w/v) in liquid formulations.

For ophthalmic application, preferably solutions are prepared using a physiological saline solution as a major vehicle. The pH of such ophthalmic solutions should preferably be maintained between 6.5 and 7.2 with an appropriate buffer system. The formulations may also contain conventional, pharmaceutically acceptable preservatives, stabilizers and surfactants.

Preferred preservatives that may be used in the pharmaceutical compositions of the present invention include, but are not limited to, benzalkonium chloride, chlorobutanol, thimerosal, phenylmercuric acetate and phenylmercuric nitrate. A preferred surfactant is, for example, Tween 80. Likewise, various preferred vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. The preferred chelating agent is edetate disodium, although other chelating agents may also be used in place of or in conjunction with it.

The ingredients are usually used in the following amounts:

| Ingredient | Amount (% w/v) |
| --- | --- |
| active ingredient | about 0.001–5 |
| preservative | 0–0.10 |
| vehicle | 0–40 |
| tonicity adjustor | 0–10 |
| buffer | 0.01–10 |
| pH adjustor | q.s. pH 4.5–7.5 |
| antioxidant | as needed |
| surfactant | as needed |
| purified water | as needed to make 100% |

The actual dose of the active compounds of the present invention depends on the specific compound, and on the condition to be treated; the selection of the appropriate dose is well within the knowledge of the skilled artisan.

The ophthalmic formulations of the present invention are conveniently packaged in forms suitable for metered application, such as in containers equipped with a dropper, to facilitate the application to the eye. Containers suitable for dropwise application are usually made of suitable inert, non-toxic plastic material, and generally contain between about 0.5 and about 15 ml solution.

The invention is further illustrated by the following non-limiting Examples.

Example 1

Figure 1:
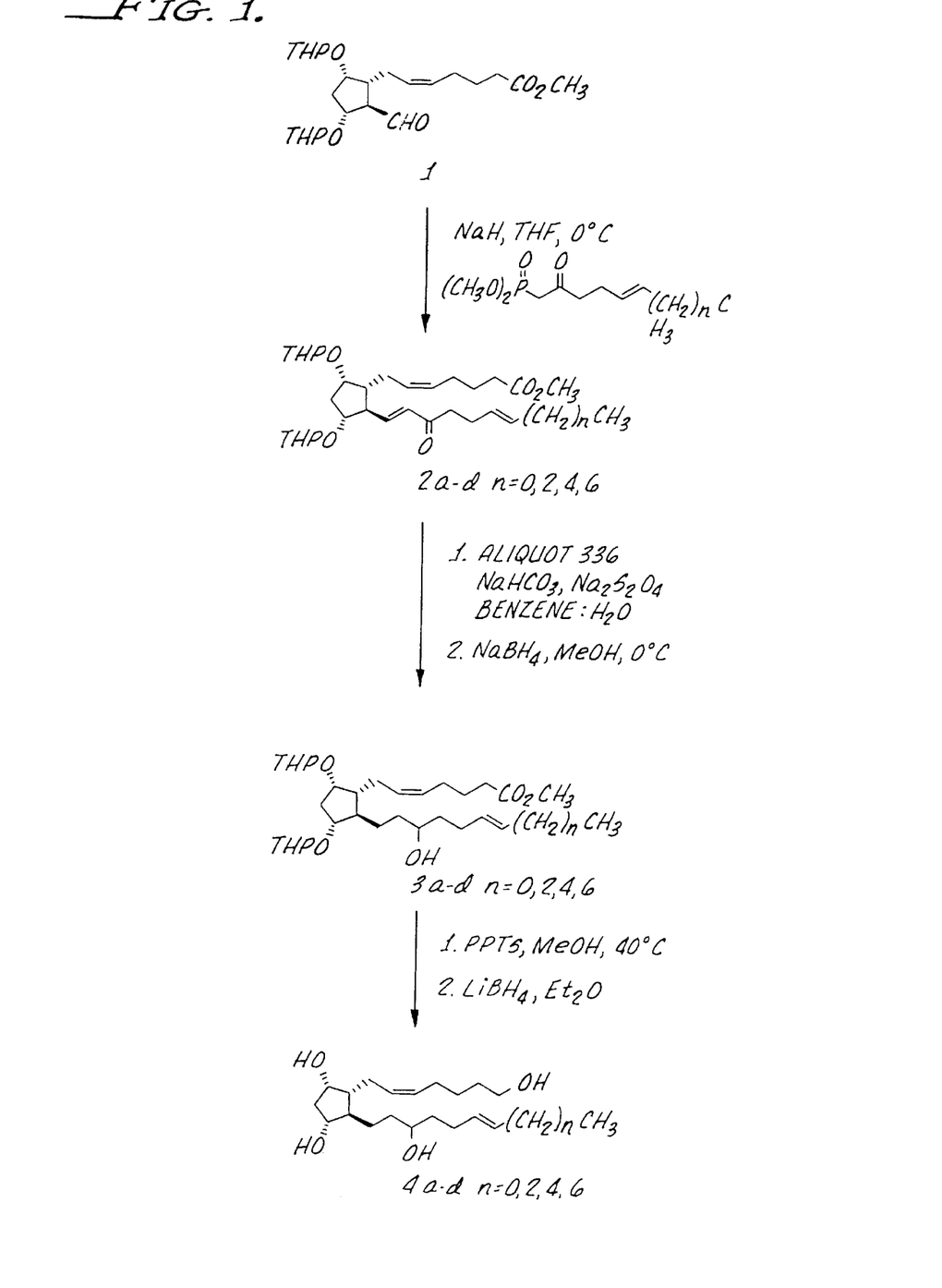
FIG. 1 is a schematic illustrating the preparation of the compounds of Examples 1 through 4.

The compound wherein THP represents tetrahydropyran, dissolved in tetrahydrofuran (THF), is reacted with $(CH_3O)_2P(O)CH_2CH_2CH_2CH\,CH\,(CH_2)_nCH_3$, wherein n is 0 or an integer of 2, 4 or 6, in the presence of NaH to yield the enone

Example 2

0.245 mmoles of the resulting enone of Example 1 is reacted with 0.074 mmol Aliquot 336, 2.209 mmol of $Na_2S_2O_4$, 4.419 mmol of $NaHCO_3$ in 6.0 mL of a 1 to 1 mixture of benzene and water at 75° C. for 1.5 h. The reaction is allowed to cool to room temperature, is diluted with ethylacetate (EtOAc), and washed with $H_2O$ and brine. The organic portion is dried over $MgSO_4$, filtered and the filtrate concentrated in vacuo. Purification by flash column chromatography (FCC) with a 4:1 mixture of hexane and EtOAc gives an 83% yield of the ketone.

Example 3

Sodium tetrahydridoborate (0.375 mmol) is added to a solution of the ketone of Example 2 (0.375 mmol) in 3.0 mL of methanol (MeOH) and cooled to 0° C. After 30 minutes, the reaction is quenched with saturated aqueous $NH_4Cl$ and allowed to warm to room temperature. The mixture is extracted with ethylether ($Et_2O$), the organic portion is dried over $MgSO_4$, filtered and concentrated in vacuo to yield the expected alcohol.

Example 4

The residue of Example 3, including the resulting alcohol, is diluted with 3.0 mL of methanol (MeOH) and pyridinium p-toluene sulfonate (PPTs) (0.362 mmol) is added. After heating to 45° C. for 16 h, the reaction is concentrated in vacuo, diluted with EtOAc and washed with 1 N HCl, saturated aqueous $Na_2HCO_3$, brine, dried over $MgSO_4$, filtered and concentrated in vacuo. Purification by FCC with a 2:1 EtOAc/hexane mixture followed by 100% EtOAc gave 83% yield of a mixture of the triol.

To a solution of the triol in anhydrous $Et_2O$ cooled to 0° C. was added lithium borohydride (0.30 mmol). After 1 h the reaction was allowed to warm to 23° C. and stirring was continued for 12 h. The reaction was quenched with 1 N NaOH, stirred for 0.5 h and extracted with EtOAc. The organic portion was separated, washed with brine, dried over $MgSO_4$, filtered and concentrated in vacuo. Purification by FCC eluded over silica gel with 100% EtOAc afforded 64% of the tetrol.

Examples 5 through 8

Figure 2:
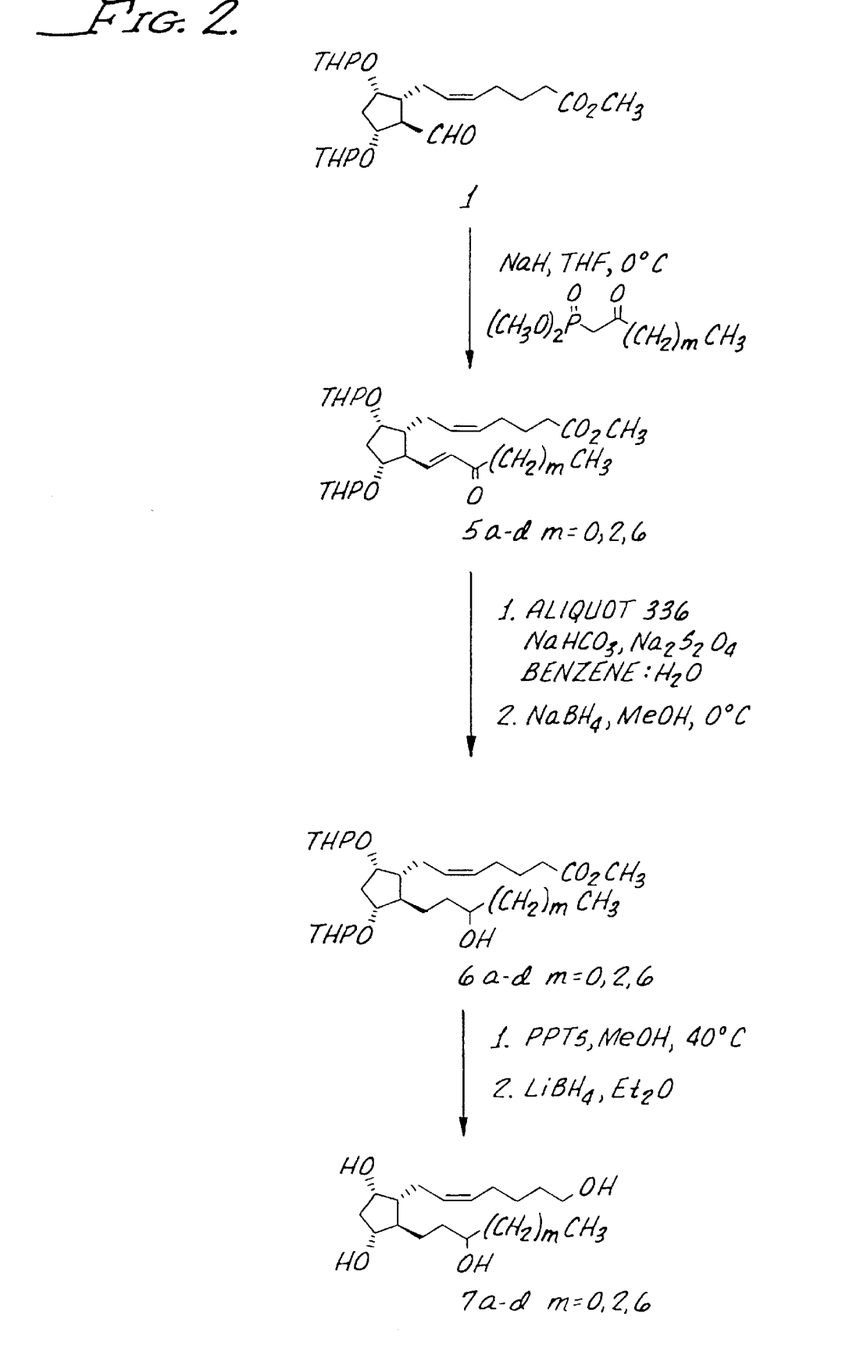
FIG. 2 is a schematic illustrating the preparation of the compounds of Examples 5 through 8.

The procedures of Examples 1 through 4 are repeated with $(CH_3O)_2P(O)CH_2C(CH_2)_mCH_3$, replacing the saturated phosphonate of Example 1 to yield

Examples 9 and 10

Figure 3:
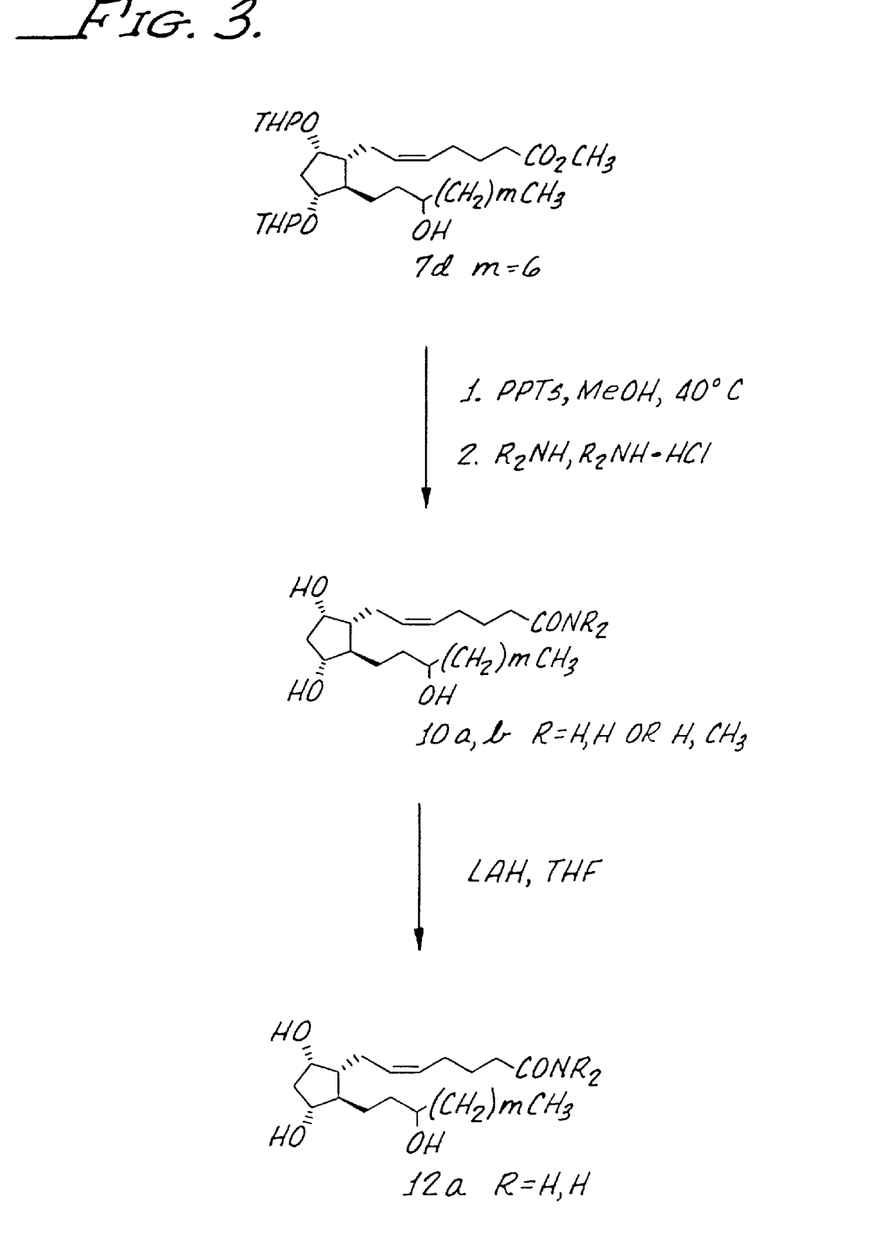
FIG. 3 is a schematic illustrating the preparation of the compounds of Examples 9 through 12.

In separate runs, ammonia gas is condensed into a tube containing either 0.126 mmoles of the ester of Example 3 or Example 7 and ammonium chloride (2.51 mmol) to a total volume of 4.5 mL. The tube is then heated to 65–70° C. for 48 h, cooled to −70° C., unsealed and allowed to slowly warm to room temperature on its own accord. The residue is dissolved in water and extracted with EtOAc. The organic portion is washed with saturated aqueous NaCl, dried $MgSO_4$, filtered and concentrated in vacuo. Purification by FCC with 100% EtOAc followed by 9:1 EtOAc/MeOH gave a 54% yield of the amide wherein R is H, respectively.

When a tertiary lower alkyl amine and/or a quaternary chloride is substituted for $NH_3$ and/or $NH_4Cl$, the corresponding 1-n-lower alkyl amide is obtained.

Examples 11 and 12

A solution of any of the amides of Examples 9 and 10 (0.183 mmol) in THF (2.0 mL) is treated with lithium aluminum hydride (LAH) (0.18 mmol) at 23° C. After 24 h the reaction is quenched with 2 N NaOH and extracted with EtOAc. The organic portions are dried over $MgSO_4$, filtered and concentrated in vacuo. Purification by FCC with 6:1: 0.1 $CH_2Cl_2$/MeOH/$NH_4OH$ gave 26% yield of the amine The effects of the compounds of the invention on intraocular pressure are determined as follows:

The compounds are prepared at 0.01 and 0.1%, by weight, concentrations in a vehicle comprising 0.1%, by weight, Polysorbate 80 and 10 mM TRIS base. Dogs are treated by administering 25 μl of the resulting solution to the ocular surface, while the contralateral eye receives vehicle as a control. Intraocular pressure is measured by applanation pneumatonometry. Dog intraocular pressure is measured immediately before drug administration and at 6 hours thereafter.

The compounds of Examples 1 through 12 are examined and found to reduce the intraocular pressure as compared to the vehicle, above.

The foregoing description details specific methods and compositions that can be employed to practice the present invention, and represents the best mode contemplated. However, it is apparent for one of ordinary skill in the art that further compounds with the desired pharmacological properties can be prepared in an analogous manner, and that the disclosed compounds can also be obtained from different starting compounds via different chemical reactions. Similarly, different pharmaceutical compositions may be prepared and used with substantially the same result. Thus, however detailed the foregoing may appear in text, it should not be construed as limiting the overall scope hereof; rather, the ambit of the present invention is to be governed only by the lawful construction of the appended claims.

What is claimed is:

1. A method of treating ocular hypertension which comprises administering to a mammal having ocular hypertension a therapeutically effective amount of a compound of formula I is wherein the hatched segments represent a bonds; the wavy segment represents an α or β bond; dashed lines represent a double bond or a single bond; X is selected from the group consisting of —OR and $N(R_2)$; Y is=O or represents 2 hydrogen radicals, provided that Y represents 2 hydrogen radicals when X is OH; R is hydrogen or a lower alkyl radical having up to six carbon atoms; $R^1$ is=O or hydroxy; m is 0, 2, 4 or 6, provided that m is not 4 when the wavy segment represents α β bond; n is 0, 2, 4 or 6; x and y are 0 or 1, provided that x is 1 when y is 0 and y is 1 when x is 0; or 9, 11 and/or 15 ester derivatives of said compound of formula I, or a pharmaceutically acceptable salt thereof.

2. The method of claim 1 wherein R is hydrogen.

3. The method of claim 2 wherein said 9, 11 and/or 15 ester derivative is a $C_1$ to $C_6$ alkyl ester derivative.

4. The method of claim 3 wherein $R^1$ is hydroxy.

5. The method of claim 1 wherein said compound is a compound of formula II

6. The method of claim 1 wherein said compound is a compound of formula III

7. The method of claim 1 wherein said compound is selected from the group consisting of:

7-[3a −5a-Dihydroxy-2-(6-hydroxy-2E-octenyl) cyclopentyl]-5Z-hepten-1-ol.

\* \* \* \* \*

UNITED STATES PATENT AND TRADEMARK OFFICE
CERTIFICATE OF CORRECTION

PATENT NO. : 6,258,844 B1
DATED : July 10, 2001
INVENTOR(S) : Garst et al.

It is certified that error appears in the above-identified patent and that said Letters Patent is hereby corrected as shown below:

Column 3,
Line 21, delete "a" and insert in place thereof -- $\alpha$ --
Line 29, delete "$\alpha$" and insert in place thereof -- a --

Column 4,
Line 13, after "C-13," insert -- or C-17 --

Column 10,
Line 62, delete "a" and insert in place thereof -- $\alpha$ --

Column 11,
Line 1, delete "$R^1$" and insert in place thereof -- $R_1$ --
Line 3, delete "$\alpha$" and insert in place thereof -- a --

Column 12,
Line 19, delete "3a-5a" and insert in place thereof -- $3\alpha$-$5\alpha$ --

Signed and Sealed this

Twelfth Day of November, 2002

*Attest:*

*Attesting Officer*

JAMES E. ROGAN
*Director of the United States Patent and Trademark Office*